(12) United States Patent
Vaudrey et al.

(10) Patent No.: US 7,457,428 B2
(45) Date of Patent: Nov. 25, 2008

(54) DOUBLE HEARING PROTECTION DEVICE

(75) Inventors: Michael A. Vaudrey, Blacksburg, VA (US); William Saunders, Blacksburg, VA (US); Yu Du, Christiansburg, VA (US); Jonathan Hager, Salem, VA (US)

(73) Assignee: Adaptive Technologies, Inc., Blacksburg, VA (US)

( * ) Notice: Subject to any disclaimer, the term of this patent is extended or adjusted under 35 U.S.C. 154(b) by 235 days.

(21) Appl. No.: 11/494,067

(22) Filed: Jul. 27, 2006

(65) Prior Publication Data

US 2008/0025524 A1    Jan. 31, 2008

(51) Int. Cl.
  *H04R 25/00* (2006.01)
(52) U.S. Cl. ........................ 381/372; 381/380
(58) Field of Classification Search ................ 381/72, 381/370, 372, 380; 181/129, 130, 135; 128/864, 128/866, 867; 2/209
See application file for complete search history.

(56) References Cited

U.S. PATENT DOCUMENTS

| 4,916,758 | A | * | 4/1990 | Jordan-Ross ................... 2/209 |
| 4,972,491 | A | | 11/1990 | Wilcox |
| 5,426,719 | A | | 6/1995 | Franks et al. |
| 5,749,373 | A | | 5/1998 | Dix |
| 6,012,812 | A | | 1/2000 | Rickards |

* cited by examiner

*Primary Examiner*—Brian Ensey
(74) *Attorney, Agent, or Firm*—Roberts Mardula & Wertheim LLC

(57) ABSTRACT

A double hearing protection system comprises a circumaural hearing protector that covers and encircles the pinnae and an earplug device that is inserted into the ear canal. The earplug portion of the system comprises a tether that is coupled to the interior of a circumaural hearing protector. The tether retracts into the earcup when both the earplug and circumaural hearing protector are worn, ensuring that the earseal against the head is not broken by the retractable tether.

15 Claims, 6 Drawing Sheets

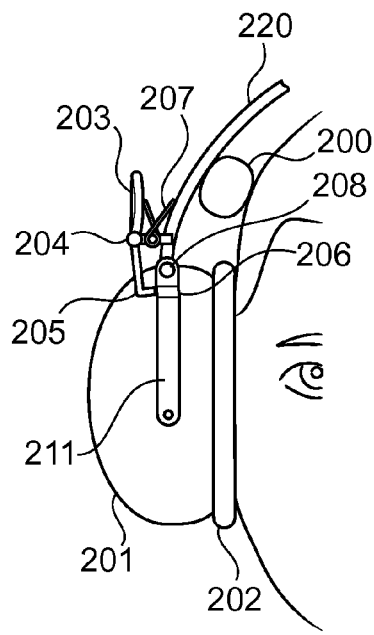
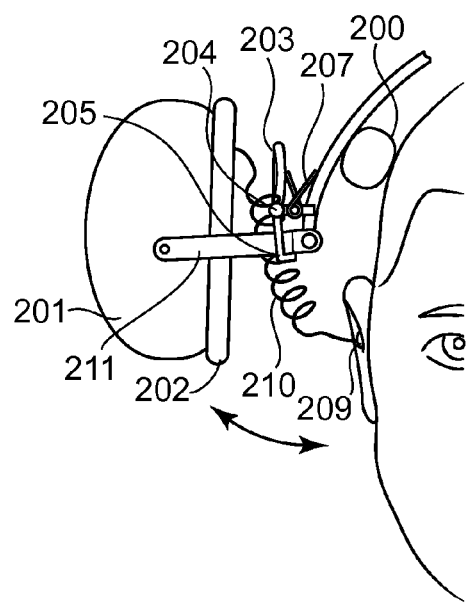
FIGURE 5A        FIGURE 5B
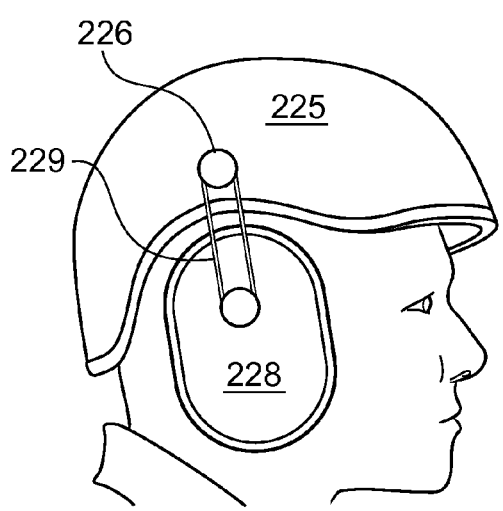
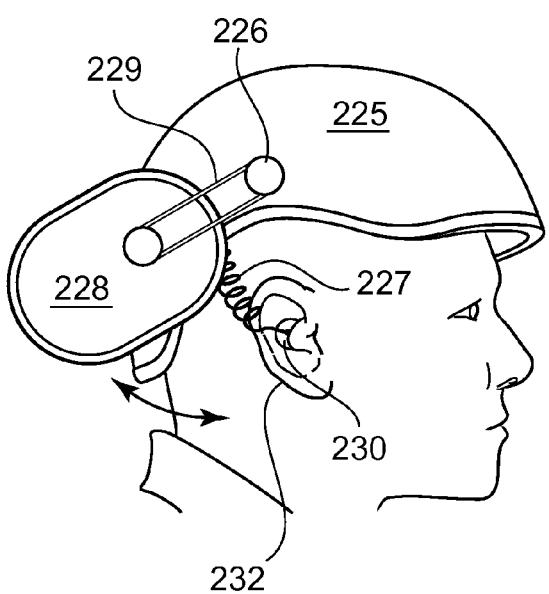
FIGURE 6A        FIGURE 6B

DOUBLE HEARING PROTECTION DEVICE

BACKGROUND

Embodiments of the present invention generally relate to hearing protection devices and more particularly relate to a hearing protection device for use in high ambient noise environments to limit the noise exposure of the individual and to help prevent long term hearing loss. Embodiment of the present invention also address specific concerns in extreme and varying noise environments pertaining to the prevention of foreign object damage (FOD) in the presence of machinery that may be damaged by loose debris, such as an aircraft engine intake.

"Double hearing protection" (DHP) implies the simultaneous use of a circumaural hearing protector that covers and encircles the pinnae and an earplug device that is inserted into the ear canal. The combination of the two hearing protectors, worn together, provides combined hearing protection that is greater than either of the hearing protectors worn individually. Embodiments of the present invention provide a method and apparatus to upgrade either of the single hearing protectors (SHP) to be used as a DHP device while also helping to avoid FOD, and preventing an opening in the seal of the circumaural device that could degrade the combined performance of the DHP device.

Extreme noise environments often require the simultaneous use of both an insert earplug device and a circumaural earcup hearing protection device to afford the maximum possible noise attenuation. Although the combination of the two hearing protectors does not result in the linear summation of the two individual hearing protectors, the combination does provide higher attenuation than either hearing protector used alone as a single hearing protector (SHP). When used in combination, the performance of the double hearing protection (DHP) system can be degraded due to a structural vibration path and/or acoustic leakage around seal between the earseal of the circumaural protector and the head.

The highest occupational ambient noise environments typically exist in close proximity to high powered jet aircraft. These occupational environments most commonly exist on the US Navy and US Air Force flight decks and flight lines. In some cases ground maintainers and other personnel frequently execute final check procedures next to jet aircraft operating at maximum augmented power settings. Ambient noise in these conditions can often reach as high as 150 dB SPL with a spectral shape that is broadband, or "pink" in frequency content. It is very unsafe, in these environments with single hearing protection, and the risk of permanent hearing loss over long term exposures is almost guaranteed. Double hearing protection solutions are better but still leave the user experiencing unsafe at-ear noise levels. There is ample evidence that the current protocol of using non-tethered foam earplugs under a large volume circumaural hearing protector (earcup) is not being effectively followed. There are several reasons for this including ineffective training and enforcement of using earplugs under the circumaural earcup. However, a predominant reason is the perceived risk of foreign object damage (FOD) in these environments, whereby a non-tethered earplug may become separated from the user and pose a risk of being ingested into an aircraft engine. This potential risk is a significant deterrent for users that seems to outweigh the equally large risk of hearing loss experienced by not wearing double hearing protection in these environments.

Embodiments of the present invention address the needs of the personnel working in these environments from a variety of perspectives including: a) assisted compliance by using pre-connected earplugs, b) cost reduction through incremental purchase of two high quality hearing protectors that can be connected to each other as needed, c) FOD prevention, d) improved double hearing protection performance through innovative tether attachment protocols that prevent breaking the seal between the earcup seal and the head, prevent a significant vibratory path between the earcup and earplug, and allow access to the earplug without removing the entire hearing and head protection assembly, and e) reducing potential snag hazards in dangerous occupational environments.

Current double hearing protector product designs do not address a double hearing protection mechanism that simultaneously prevents FOD and offers the maximum possible DHP performance. U.S. Pat. No. 5,749,373 issued to Dix (herein, "Dix") and U.S. Pat. No. 6,012,812 issued to Rickards (herein, "Rickards") describe the use of a tether mechanism with small earplug devices to prevent FOD loss of the earplug, or assisted compliance. Dix presents a headband connecting two earplugs together, with an additional "breakaway" cord. This design maintains the banded earplugs hearing protector around the neck using the cord to allow the user to easily don and doff the headband and hearing protection as needed, without worrying about FOD or misplacing the hearing protector. The design describes a means by which the cord can break away from the hearing protector should the headband become entangled in any dangerous machinery, to avoid pulling the user in afterward. However, Dix fails to teach or describe double hearing protection, or the ability to secure the tether itself from becoming a snag hazard. Furthermore, the invention described in Dix cannot be used with a circumaural hearing protector because both the headband and tether assemblies will cause a leak in the earseal of the circumaural earcup.

In a similar way, Rickards describes a tether assembly to prevent FOD for an earplug but the earplug assembly is attached to safety glasses. Rickards does not teach or describe double hearing protection.

U.S. Pat. No. 5,426,719 issued to Franks et. al. (herein, "Franks") describes a hearing protector/communication system. In one embodiment a headset is disclosed and in another embodiment earplugs are disclosed. Franks does not teach or disclose the use of simultaneous earplug and earcup hearing protection, or the design of a tether between the two systems to prevent FOD or facilitate optimum performance. A cord to deliver audio signals is described, but the cordage is not secured in any way to a headset and would in fact create a leak if it were to be used in conjunction with a headset or circumaural hearing protector device.

U.S. Pat. No. 4,972,491 issued to Wilcox (herein, "Wilcox") describes using an earplug and a headset in conjunction with each other. Wilcox also describes delivering communications to the earplug and ensuring that the earplug is connected to the earcup. The earplug device is automatically placed or located on the ear canal while donning the hearing protection system. In double hearing protection systems, in high ambient noise environments, best performance is achieved when the earplug is properly inserted and inserted deeply into the ear canal. Shallow or misplaced earplugs will not offer the desired performance. In addition, the automatic placement of the earplug described by Wilcox is neither practical nor possible to achieve with deep insert earplug devices. The connection used by Wilcox in attempting to place the earplug device in the ear canal is a relatively rigid connection between the earcup and earplug. This connection will cause vibration motion induced by high ambient noise environments, to translate from the external earcup directly through to the earplug, effectively bypassing the benefit of the double hearing protection concept. Finally, the goal of automatic placement of the earplug implicitly anticipates the need for access to the earplug through the headset. Wilcox attempts to achieve this access by making it possible to place the earplug by placing the earcup. This is not possible for a wide population of individuals with different ear canal geometries and with the deep circuitous insertion required by many custom molded earplugs or the rolling required by foam earplugs, when high levels of protection are needed or desired. By attempting to accomplish the automatic placement of the earplug from within the earcup, Wilcox by default, precludes the ability to manually access the earplug for placement in the ear canal. This directly teaches away from the invention disclosed herein, by disallowing manual access to placement of the earplug, one embodiment of this invention.

What would be useful would be a double hearing device that simultaneously prevents FOD and offers the maximum possible DHP performance.

SUMMARY

An embodiment of the present invention is a double hearing protection (DHP) device for use in high ambient noise conditions comprising an ear canal insert device (earplug) and a circumaural hearing protector (earcups) that are used simultaneously with each other. In this embodiment, the earplug is connected to the interior of the earcup through a non-rigid tether so as to prevent foreign object damage as further described below. The tether is retracted into the earcup to prevent a broken earseal. Retraction of the tether also prevents possible snag hazards posed by exposed tethers. The non-rigid tether does not conduct sound. Therefore, sound received from the earcup is not translated to the earplug through conduction through the tether. In yet another embodiment of the present invention, manual placement of the earplug is facilitated by means that allow the earcup to move out of the way while the headset remains on a user's head. By way of illustration and not as a limitation, in an embodiment of the present invention, the earcup is hinged so as to permit access to the pinna without removing the entire circumaural hearing protector assembly.

In another embodiment of the present invention, the tether attachment means comprises an electronic connector and the tether is a coiled multi-conductor cable. In this embodiment, the DHP may include active noise reduction, 1-way or 2-way communications through the earplug device, or ambient sound pass-through similar to a hearing aid device.

It is therefore an aspect of the present invention to provide a means by which to achieve double hearing protection attenuation performance without rigidly connecting the earplug to the earcup hearing protector that would otherwise sacrifice performance.

It is another aspect of this invention to provide a means by which to prevent foreign object damage in extreme noise environments by ensuring that small earplugs are connected to the earcups in a semi-permanent fashion.

It is another aspect of the present invention to permit the replacement of attached earplugs in a double hearing protector while also preventing the risk of foreign object damage.

It is a further aspect of the invention to avoid sacrificing DHP performance by including a retractable cable or tether means attached to the inside of the earcup and outside of the earplug to prevent the tether from breaking the seal of the circumaural hearing protector against the head.

It is a further aspect of this invention to illustrate a practical means for manufacturing a high strength replaceable attachment between a tethered earplug and earcup assembly that maintains comparatively high tensile strength in normal pulling directions.

It is another aspect of this invention to illustrate means by which the tethered double hearing protection device may be easily donned by allowing the earcups to move independent of the headband on the circumaural protector, permitting manual access to the earplugs.

It is a further aspect of this invention to provide a similar means to offer a retractable and replaceable earplug device for use with a double hearing protection system that operates as an integral component of an electronic hearing assistance and protection means including talk-through-the-ear, communications, and active noise reduction through the earplug.

These and other aspects of the present invention will become apparent to those skilled in the art from a review of the descriptions contained herein.

In an embodiment of the present invention, a double hearing protection device comprises a circumaural hearing protector having an interior attachment point, an earplug device for manual insertion into an ear canal of a user, and a tether assembly. In an embodiment of the present invention, the circumaural hearing protector comprises an earcup that covers a pinna of a user. In another embodiment of the present invention, the earplug device is a passive hearing protection device. In an alternative embodiment of the present invention, the earplug device provides active noise control in the ear canal.

The tether assembly comprises an earplug termination and an earcup termination. The tether assembly is attaches to the earplug device at the earplug termination, attaches to the interior attachment point of the earcup at the earcup termination, and retracts for storage inside the earcup when the earcup is placed over the earplug device and over the pinna of the user. In another embodiment of the present invention, the tether assembly is coiled. In yet another embodiment of the present invention, the tether assembly comprises a strength member. By way of illustration and not as a limitation, the strength member may be aramid or Kevlar.

In an embodiment of the present invention, the interior attachment point of the circumaural hearing protector comprises a spherical chamber. In this embodiment, the earcup termination of the tether assembly comprises a spherical termination that mates with the spherical chamber.

In another embodiment of the present invention, the interior attachment point of the circumaural hearing protector comprises a first molded feature and the earcup termination of the tether assembly comprises a second molded feature. In this embodiment, the second molded feature mates with the first molded feature. The earplug termination comprises a third molded feature comprising a bend relief. The third molded feature is adapted for bonding to the earplug device. In yet another embodiment of the present invention, the tether assembly comprises a strength member that bonds to the second molded feature and to the earplug device.

In another embodiment of the present invention, the tether assembly comprises an electrical conductor that permits the earcup and the earplug device to exchange electrical signals. In this embodiment, the earcup termination comprises a first electrical connector and the interior attachment point comprises a second electrical connector that mates with the first electrical connector.

In still another embodiment of the present invention, the electrical signals comprise audio signals generated by an audio source in the earcup. In this embodiment the earplug device comprises a transducer to receive the audio signals. By way of illustration and not as a limitation, the electrical audio source may be a microphone, a radio, an intercom, an amplifier, or a sound conditioning circuit.

In an embodiment of the present invention, the circumaural hearing protection device further comprises a headband to retain the earcup in a position that encircles the pinna of the user. In this embodiment, the earcup further comprises an external attaching mechanism adapted for connecting the earcup to the headband. The external attaching mechanism moves the earcup into a first position that covers the pinna of the user and locks the earcup in the first position, and moves the earcup into a second position displaced from the pinna of the user without removing the headband and locks the earcup in the second position.

In another embodiment of the present invention, the external attaching mechanism comprises a hinge and the earcup is adapted to rotate upward relative to the pinna to the second position. In yet another embodiment of the present invention, the external attaching mechanism comprises a hinge and the earcup is adapted to rest orthogonally from the pinna in the second position.

DESCRIPTION OF THE DRAWINGS

FIGS. 5A and B illustrate the up and down positions of a hinge applied to an earcup wherein the earcup is held in the up position but locks in the down position to provide accessibility to the earplug according to an embodiment of the present invention.

FIGS. 6A and B illustrate an earcup that is mounted to a hardhat with a rotational feature allowing the earcup to be moved away from the ear to allow easy insertion of a tethered earplug according to an embodiment of the present invention.

DETAILED DESCRIPTION

The following terms are used in the description that follows. The definitions are provided for clarity of understanding:

| | |
|---|---|
| DHP: | Double hearing protection; a device in which an ear canal insert device (earplug) and a circumaural hearing protector (earcups) are used simultaneously. |
| Donning: | refers to the action of inserting the earplugs into the ear canal and placing the circumaural hearing protector over the pinna and the earplugs, to achieve double hearing protection. |
| Doffing: | refers to the action of removing a hearing protection device. |
| FOD: | Foreign object damage; refers to an event in which a small piece of equipment may be inadvertently ingested into sensitive machinery causing damage. |
| SHP: | Single hearing protection; a device in which either an ear canal insert device (earplug) or a circumaural hearing protector (earcups) is used. |

An embodiment of the present invention is a double hearing protection (DHP) device for use in high ambient noise conditions comprising an ear canal insert device (earplug) and a circumaural hearing protector (earcups) that are used simultaneously. In this embodiment, the earplug is connected to the interior of the earcup through a non-rigid tether so as to prevent foreign object damage. The tether is retracted into the earcup to prevent a broken earseal. Retraction of the tether into the earcup also prevents the possibility of the tether becoming a snag hazard. The non-rigid tether does not conduct sound. Therefore, sound received from the earcup is not translated to the earplug through conduction through the tether. In yet another embodiment of the present invention, manual placement of the earplug is facilitated by means that allow the earcup to move out of the way while the headset remains on a user's head. By way of illustration and not as a limitation, in an embodiment of the present invention, the earcup is hinged so as to permit access to the pinna without removing the entire circumaural hearing protector assembly.

In another embodiment of the present invention, the tether attachment comprises an electronic connector and the tether is a coiled multi-conductor cable. In this embodiment, the DHP may also include active noise reduction, 1-way or 2-way communications through the earplug device, or ambient sound pass-through similar to a hearing aid device.

Figure 1:
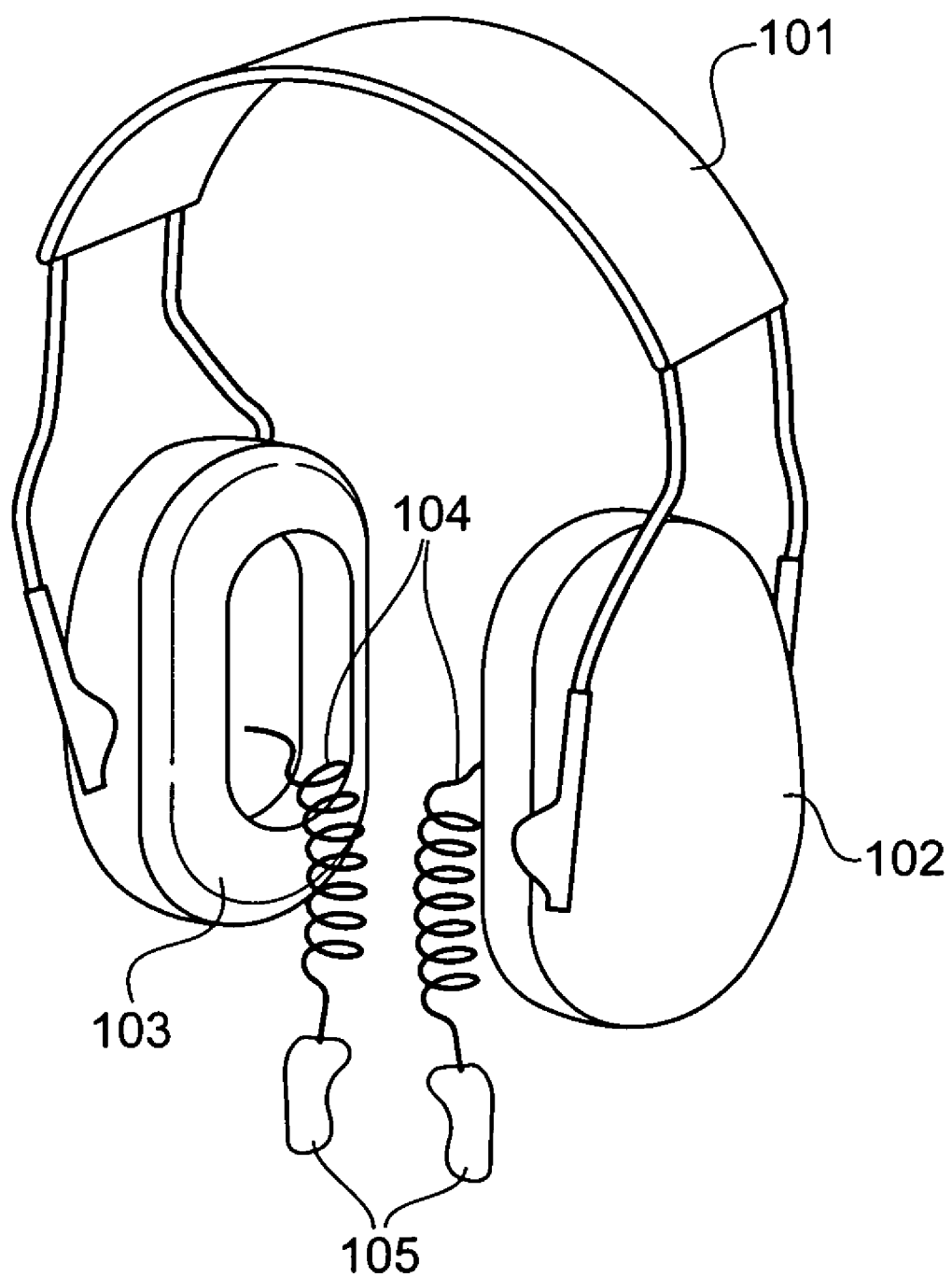
FIG. 1 illustrates a double hearing protection (DHP) device comprising a circumaural hearing protector and a pair of custom molded earplug devices retractably tethered to the inside of the earcups according to an embodiment of the present invention.

FIG. 1 illustrates a double hearing protection (DHP) device comprising a circumaural hearing protector and a pair of custom molded earplug devices retractably tethered to the inside of the earcups according to an embodiment of the present invention. The headband 101 connects the earcups 102 and earseals 103 to form the circumaural portion of this hearing protector. The earplugs 105 are connected to the inside of the earcups 102 by retractable tethers 104. The earplugs may be any type of earplug including without limitation, custom molded earplugs, disposable foam earplugs, multiple flanged plastic earplugs, etc. The retractable tether is typically a coiled strength member intended to be attached at the earplug and at the earcup. In this embodiment of the present invention, the attachment on the earcup 102 is removable and the attachment on the earplug 105 is permanent. However, this is not meant as a limitation. In an alternate embodiment of the present invention, the attachment on the earplug side may also be removable. The retractable tether may be made in a variety of ways including a passive tether (without electrical conductors, but with a strength member), or an electrical cable comprising electrical conductors for allowing any number of communication or active noise reduction functions that may be delivered through the earplug assembly.

Figure 2:
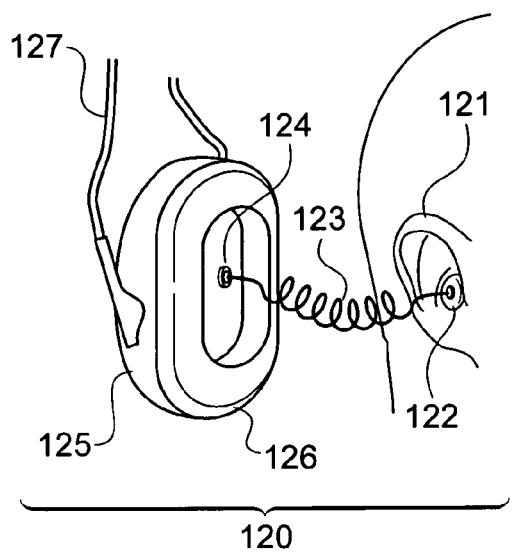
FIG. 2 illustrates a DHP device donned with the earplug in place and the circumaural hearing protector being placed on top of the ear according to an embodiment of the present invention.

FIG. 2 illustrates a DHP device donned with the earplug in place and the circumaural hearing protector being placed on top of the ear according to an embodiment of the present invention.

As illustrated in FIG. 2, an earcup 125 is placed over a user's pinna (outer ear) 121 and an earplug 122 is inserted into the ear canal. A tether 123 is connected to a tether attachment point 124 on the inside of the earcup 125 through a means described below. The headband 127 applies normal force to the side of the head through the earcup 125 causing the earseal 126 to encircle the user's pinna 121 and provide an acoustic seal. The earseal 126 maximizes the performance of the earcup portion of the DHP device 120. If the seal formed by earseal 126 is broken, or if earseal 126 is not maintained against the head, the combined performance of the DHP device 120 may be compromised.

The retractable tether 123 performs two functions in this scenario. It provides a means by which to prevent FOD from an otherwise significant FOD hazard (the earplug 122) and it retracts into the earcup 125 to prevent the tether 123 from breaking the seal and compromising the attenuation performance of the DHP device 120.

In an embodiment of the present invention, the SHP circumaural hearing protectors are upgradeable to become a DHP device. The upgradeability is accomplished by providing an earplug with retractable tether that acts as a strength member and that can be attached to the inside of the appropriately equipped circumaural hearing protector. The circumaural hearing protector is designed to provide sufficient passive noise attenuation in certain low to medium ambient noise environments where single hearing protection is prescribed. The circumaural hearing protector, however, is equipped with an attachment mechanism inside the earcup 124 that does not compromise its performance as a single hearing protector, but allows future attachment of a tethered earplug that has been designed to connect to that attachment mechanism. This allows the end user to alternately attach the earplug to the interior of the earcup to use the system as a double hearing protection system or use either as a single hearing protection system.

In another embodiment of the system, the earplug 122 is attached to the attachment point 124 of the earcup 125 without the need for a tool, but is attached in a way that is difficult to remove, or cannot be accidentally removed without excessive force. This allows for the upgradeability of the earcup system to a double hearing protection system to prevent FOD and offer the best double hearing protection performance possible with a coupled system. The latter is achieved by providing an attachment mechanism that does not act as a significant vibratory path and does not interact with the ear seal 126 of the circumaural earcup 125 surrounding the pinna 121.

Figure 3:
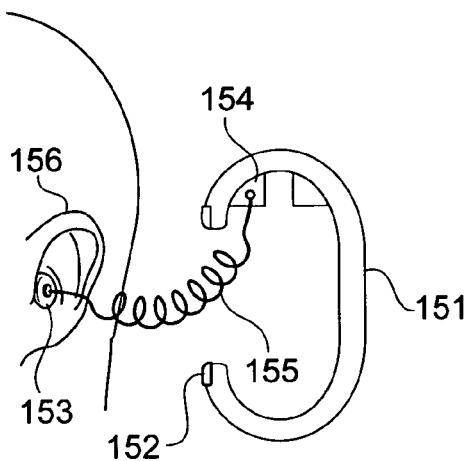
FIG. 3 illustrates a sectional view of a DHP device illustrating a circumaural hearing protector placed over the ear and a tether retracting into the earcup according to an embodiment of the present invention.

FIG. 3 illustrates a sectional view of a DHP device illustrating a circumaural hearing protector placed over the ear and a tether retracting into the earcup according to an embodiment of the present invention. Earplug 153 is inserted in the user's ear. As earcup 151 is placed over the user's pinna 156, the retractable tether 155 withdraws into the earcup 151 so as not to interfere with the earseal 152 against the user's head. The tether attachment 154 is located inside the earcup 151 and provides a means by which to attach the earplug tether 155 to the interior of the earcup 151 in a location and manner to prevent the earplug tether 155 from interfering with the earseal 152, but be sufficiently compact to not interfere with the pinna 156. In addition, the tether attachment point 154 inside the earcup 151 does not interfere with the performance of the earcup 151 assembly when used as a single hearing protector. In an embodiment of the present invention, the earcup 151 and circumaural headset assembly (not illustrated) comprise an attachment point 154 that permits the earplug 153 to be attached and removed thereby allowing the circumaural headset assembly (not illustrated) to be used as a high performance circumaural headset system, independent of the tethered earplug 153 subsystem. This permits this low cost circumaural hearing protector to be upgraded in the future to a high performance double hearing protection system that still recognizes the need for FOD prevention and a secure ear seal against the user's head for maximum performance.

Another aspect of this particular embodiment is that tether 155 forms a non-rigid connecting member between the earcup and earplug. When wearing double hearing protection systems, the performance limitations (in addition to the seal mentioned earlier) are controlled by any vibratory path between the earcup and earplug that may exist. Vibratory energy collected from the earcup, exposed to the ambient noise, translates to acoustic energy as a radiator inside the earcup. However, if the inside of the earcup 151 is rigidly connected to the outside of the earplug 153 that creates a vibratory path that can cause translational motion (vibration) of the earplug. The vibration of the earplug 153 will then in turn create acoustic energy inside the ear canal, thus limiting the attenuation performance of the DHP system. In the present invention, the tether 155 does not provide a rigid or semi-rigid vibratory path between the earcup and the earplug. By connecting the earplug 153 to the earcup 151 through a coiled, energy absorbing flexible tether, this vibratory path is significantly reduced, allowing maximum DHP performance.

Figure 4:
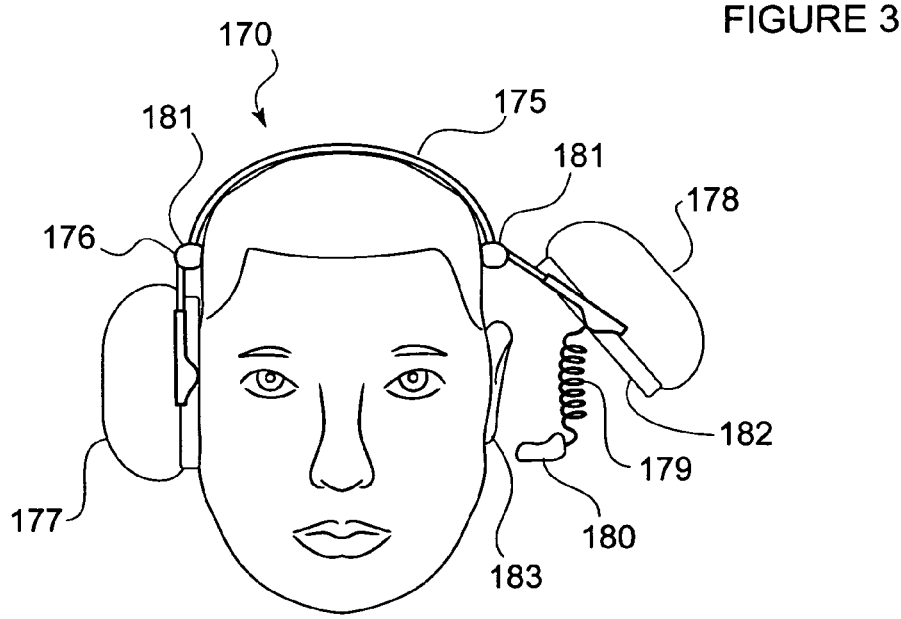
FIG. 4 illustrates an earcup that can be moved out of the way of the ear without removing the circumaural headband so as to allow for easier insertion of an earplug according to an embodiment of the present invention.

FIG. 4 illustrates an earcup that can be moved out of the way of the ear without removing the circumaural headband so as to allow for easier insertion of an earplug according to an embodiment of the present invention. In this embodiment, headband system 175 is designed in such a way as to permit easy donning and doffing the DHP system 170. Referring to the left portion of DHP system 170, earplug 180 is connected to the interior of the earcups 178 using a retractable tether 179. The retracted length of the tether 179 is able to pull completely into the earcup 178 when it is donned, as illustrated by FIG. 3, to prevent interference with the earseal 182. The retractable tether 179, as it pulls into the earcup 178, is enclosed in the earcup 178. In hazardous environments both FOD and snag hazards are serious concerns for safety. By allowing the retractable tether 179 to be completely enclosed in the earcup 178, the earplug tether 179 poses no new snag hazard. The right portion of DHP system 170 comprises a retractable tether that is connected to an earplug (not illustrated for clarity) and that is enclosed by earcup 177.

Because the extended tether dimension is constrained by the contractility of the material that is used to form the tether 179, it may be difficult in certain circumstances to properly insert the earplug 180 into the ear canal as determined by the design of earplug 180. For example, for foam earplugs and custom molded earplugs, both hands are often used to move the pinna and insert the earplug. The earplug will typically need to be rotated and carefully maneuvered into the canal to ensure proper seating and depth, a process that is not easily automated. The present invention addresses this problem as explained below.

In the embodiment illustrated in FIG. 4 relative to one side of a DHP system 170, the earcup 178 and earseal 182 can be moved out of the way of the pinna 183 and ear canal (not illustrated) to allow convenient access for manually placing the earplug 180 in the ear canal, using both hands if necessary. A locking hinge 176 is used to rotate the earcup 178 away from the head while keeping the headband 175 in place on the head via the lateral headband cushion 181. While FIG. 4 illustrates the rotation of earcup 178, earcup 177 is configured to move in the same manner.

FIGS. 5A and B illustrate the up and down positions of a hinge applied to an earcup wherein the earcup is held in the up position but locks in the down position to provide accessibility to the earplug according to an embodiment of the present invention. Referring to FIG. 5A, earcup 201 and an earseal 202 are suspended in a hoop 211 from the headband 220 resting on the headband cushion 200. The hoop 211 is hinged at pivot point 208 at the headband 200 location to allow it to move away from the head and ear. FIG. 5A illustrates the earcup 201 in the latched down position and FIG. 5B illustrates the earcup 201 in the latched up position, revealing the pinna 222 and earplug 209 tethered 210 to the inside of the earcup 201. In the down position the earcup 201 is locked in place by a latch 205 that engages member 206. Latch 205 pivots away from member 206 when lever 203 is manually pressed and rotated to release the lock 205 from the member 206. The latch 205 is held in a locked position by the force of spring 207 pressing against lever 203. When the latch is released, the earcup 201 and hoop 211 are free to move about the pivot point 208.

Referring to FIG. 5B, when rotated approximately 90 degrees away from the head, the latch 205 can engage the other side of the member 206 and the spring 207 load applied to the lever 203 rotates the latch 205 about the hinge 204 to engage the lock into the horizontal position. When the earcup 201 is rotated away from the head the reaction force of the headband 220 is borne by the headband cushion 200 which rests against the head above the pinna 222. The tether 201 permits this movement without removing the earplug 209 from the ear. This will enable some level of reduced protection, ear cooling, and simplified don/doff actions for the earplug. It is also an embodiment of the present invention that the locking of the earcup in the "up" position is not required, but instead the earcup is free to pivot, and lock in the "down" position only.

As will be appreciated by those skilled in the art, any number of means may be used to move the earcup components of a DHP device to provide access to the ear canal and to the earplug components without departing from the scope of the present invention. By way of illustration and not as a limitation, FIGS. 6A and B illustrate an earcup that is mounted to a hardhat with a rotational feature allowing the earcup to be moved away from the ear to allow easy insertion of a tethered earplug according to an embodiment of the present invention. The construction helmet 225 is equipped with an earcup 228 and partial headband 229 that rotates the earcup away from the ear using a hinge 226. In this embodiment, the tethered double hearing protector is installed on this mechanism to allow access to the earplug 230 connected by the retractable tether 227 when the earcup is moved away from the pinna 232 as illustrated in FIG. 6B. As before, this configuration provides the ability to upgrade a SHP earcup to a DHP device that provides a means for double hearing protection compliance, illustrates a means for accessing the ear under the earcup by moving the upgradeable earcup away from the ear, provides a means that prevents FOD hazards present with non-tethered earplugs and that prevents a tether from breaking the ear seal of the earcup system which would reduce attenuation performance.

Figure 7:
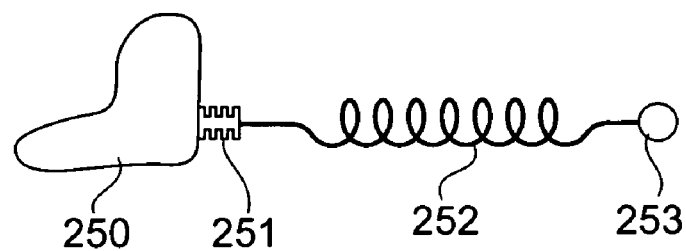
FIG. 7 illustrates an assembly comprising an earplug and a tether according to an embodiment of the present invention.

FIG. 7 illustrates an assembly comprising an earplug and a tether according to an embodiment of the present invention.

In an embodiment of the present invention, earplug 250 is a custom molded earplug, manufactured specifically for one individual. Such earplugs last longer and can perform as well as foam earplugs if designed properly. However, this is not meant as a limitation. The structures described in reference to FIG. 7 may be used with foam earplugs, or other types of earplugs without departing from the scope of the present invention.

The earplug 250 in FIG. 7 is connected to the retractable tether 252 through a molded bend relief 251 to prevent the tether from pulling away from the earplug, or cutting into the earplug during flexible movement of the tether.

As illustrated in FIG. 7 and in one embodiment of the present invention, tether 252 does not comprise electrical conductors. However, as will be appreciated by those skilled in the art, and in yet another embodiment of the present invention, a tether comprising electrical conductors does not exceed the scope of present invention. By way of illustration, retractable tether 252 comprises one or more insulated electrical conductors that may be used for a variety of purposes. In one embodiment of the present invention, the earplug 250 serves as a one way communication device that comprises a speaker (not illustrated) built into the earplug 250. Two electrical conductors would be used to convey a signal from the earcup (see FIG. 2, 125) to the speaker terminals to drive the speaker. As will be appreciated by those skilled in the art, an earcup (see FIG. 2, 125) may comprise a variety of devices that produce audio signals. By way of illustration and not as a limitation, an audio signal may be generated by a microphone, a radio, an intercom, and audio signal conditioning circuit, to name a few.

In another embodiment of the present invention, a microphone (not illustrated) inside the earplug 250 may also be used to sense the user's voice and enable 2-way communications when used with the speaker (not illustrated). The earplug microphone may require voltage, ground, and signal conductors, or may only require signal and ground conductors.

In yet another embodiment of the present invention, an external microphone (not illustrated) may be used to sense the ambient sound that can be delivered to the speaker through an appropriate processing means known in the art. In this embodiment, a plurality of conductors may be used for the external microphone. Any combination of these embodiments may be possible depending on the intended usage, and will determine the number and type of conductors that are used in the retractable electrical cable.

In an embodiment of the present invention, the electrical connector attaches to the inside of the ear cup using a multi-conductor connector. By way of illustration and not as a limitation, a "LEMO" style connector may be use. In yet another embodiment of the present invention, the electrical conductor, whether shielded or unshielded, is chosen to facilitate retraction of the tether 252 into the earcup (see FIG. 2, 125). By way of illustration and not as limitation, a shielded conductor with a spiral-wrapped shield that facilitates reliable coiling of tether 252 may be used. As will be appreciated by those skilled in the art, a tether 252 constructed from an electrical conductor, whether shielded or otherwise, that provides acceptable retraction is within the scope of the present invention.

In still another embodiment of the present invention, a tether 252 with or without electrical conductors comprises a strength member of aramid, Kevlar, or similar fibers (not illustrated) that ensure that the load stress is not placed on the flexible jacket material (rubber, polyurethane, or other plastic or rubber compound to protect the strength member and electrical conductors) of the tether 252 or, if applicable, the electrical conductors. The coil dimensions depend on the desired retracted length and extended length of the tether 252 assembly, as well as the diameter of the tether 252.

Additionally, in environments in which vibration is a factor, an embodiment of the present invention utilizes a small diameter material for tether 252 for improved vibration translation resistance. In this embodiment, the small diameter of the tether 252 would not interfere with the ear, will easily retract into the earcup, and would provide ample access for inserting an earplug from a donned headset.

Figure 8:
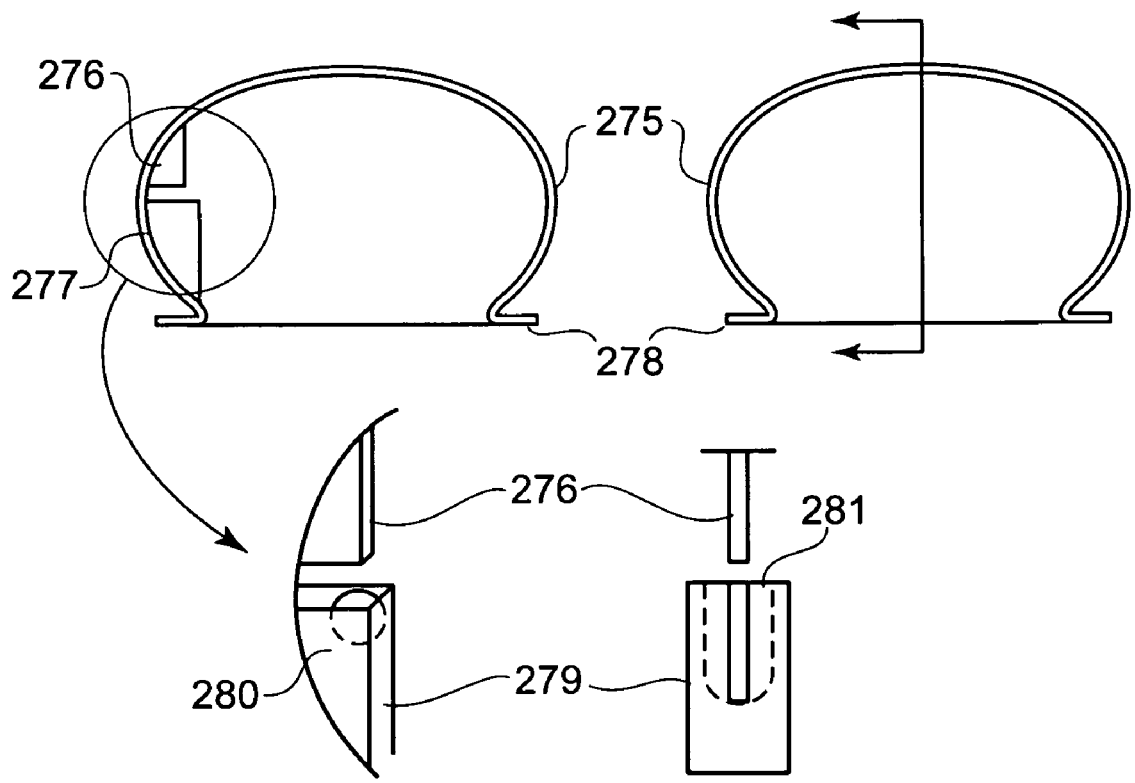
FIG. 8 illustrates a cross sectional and isometric view of a retention feature inside an earcup that mates with a retention feature on an earplug tether according to an embodiment of the present invention.
Figure 9:
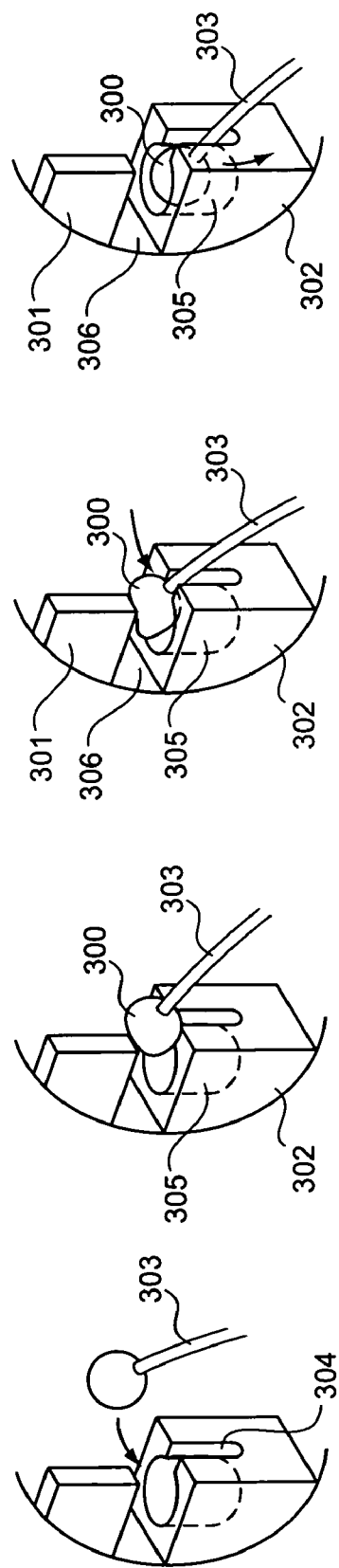
FIG. 9 illustrates a multi-step view of the retention end of an earplug tether being inserted into an earcup retention feature according to an embodiment of the present invention.

The distal end of the tether 252 may be terminated in an assembly that is designed to interface with the internal mechanism of the earcup (illustrated in FIGS. 8 and 9). As illustrated in FIG. 7, the end of the tether 252 is terminated with a sphere that is over molded onto the tether in a process that is described further in the discussion of FIG. 11 that follows below. However, this is not meant as a limitation. Other termination systems may be used without departing from the scope of the present invention.

FIG. 8 illustrates a cross sectional and isometric view of a retention feature inside an earcup that mates with a retention feature on an earplug tether according to an embodiment of the present invention. Earcup 275 comprises a lip 278 for an earseal and bosses 276 and 277 are installed on each half of the earcup assembly. The earcup is typically assembled in two halves since the injection mold tooling cannot easily release molds with overhangs. In this embodiment the bottom half includes boss 276 that is designed as a retainer and the top half (closest to the ear) comprises boss 277, 279 that has a chamber 280 for insertion of a sphere (see, FIG. 7) and a slot for the tether (FIG. 7, 252) to reside. The sphere is inserted and captured into the chamber and slot at location 281.

FIG. 9 illustrates a multi-step view of the retention end of an earplug tether being inserted into an earcup retention feature according to an embodiment of the present invention. The distal end of the tether 303 and sphere 300 is inserted into chamber 305 passing boss 301 and entering boss 302. The clearance 306 between boss 301 and 302 is less than the diameter of the sphere 300. Therefore the sphere is made of a material that is compliant enough to compress and pass into the chamber but will not fall out without being forcibly removed. The slot 304 allows the tether 303 to drag the sphere 300 into the bottom of the chamber 305. This mechanism may be improved and modified in any number of ways without departing from the scope of the present invention. For example, for custom molded earplugs it may be desirable to insert the left earplug into the left earcup and the right earplug into the right earcup. In this case, the sphere may be modified to be a pyramid or a cube for one side and another shape for the other side to ensure a keyed assembly process.

In addition, rather than a passive connection point, any number of detachable electrical connectors may be used to attach the earplug to the inside of the earcup, if the earplug is using active signals for one or two-way communication, or active noise reduction. This connection may be a shielded, circular connection with a retractable cable that still prevents FOD, and improves double hearing protection performance. In any case, the attachment point is designed without significantly compromising fit rate or attenuation of the single hearing protector circumaural headset. This ensures that the circumaural headset system may be used singly, or in combination with tethered earplugs, achieving the best performance with both device configurations. The primary method for ensuring minimal impact of the attachment mechanism in the earcup for single hearing protection is to minimize the internal earcup volume occupied by the boss fixtures for the attachment point.

Figure 10:
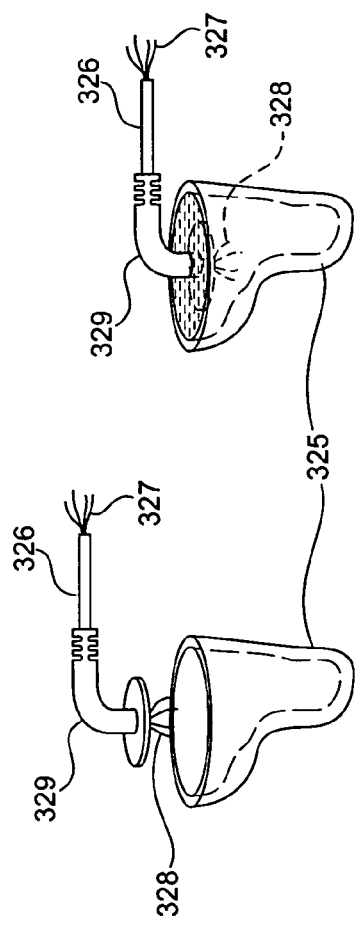
FIG. 10 illustrates a bend relief being molded into an earplug with a strength member of a tether being bonded to the earplug material for maximum retention and strength according to an embodiment of the present invention.
Figure 11:
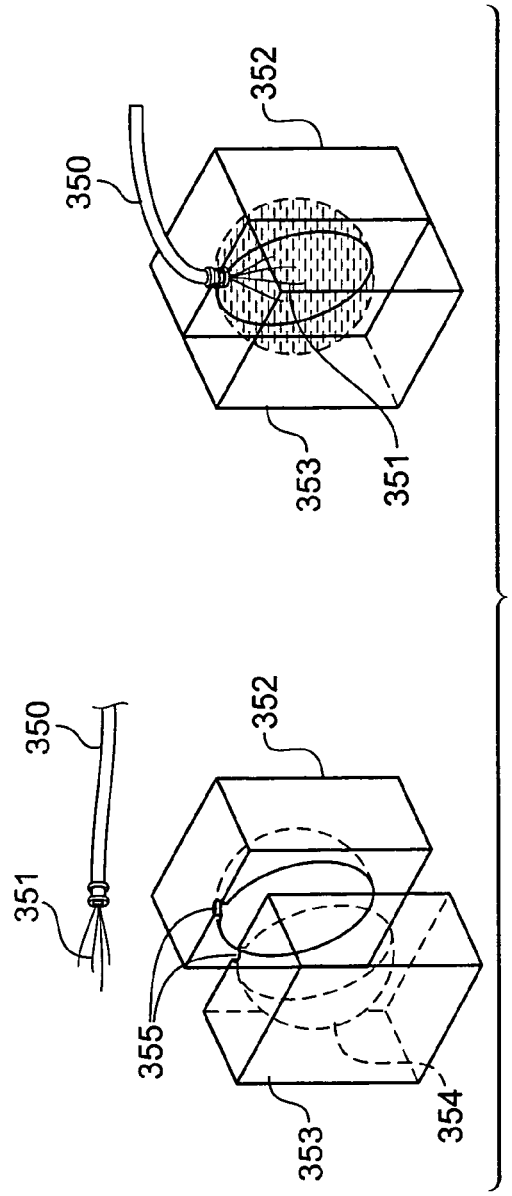
FIG. 11 illustrates a retention sphere end of a tethered earplug assembly being molded to a strength member of a tether for maximum strength according to an embodiment of the present invention.

FIG. 10 illustrates a bend relief being molded into an earplug with a strength member of a tether being bonded to the earplug material for maximum retention and strength according to an embodiment of the present invention. FIG. 11 illustrates a retention sphere end of a tethered earplug assembly being molded to a strength member of a tether for maximum strength according to an embodiment of the present invention.

Referring to FIG. 10, the custom molded earplug 325 is made using a casting process where the earplug material is in a liquid or relatively fluid form prior to curing, in order to achieve the custom molded shape. Prior to curing, the bend relief 329 with tether 326 installed or over molded is placed in the uncured earplug material. The strength members 328 and 327 of tether 326 are immersed in the uncured earplug material to provide a bond strength whereby any stress from the tether is translated directly to the earplug material. This is advisable for cases where the custom molded earplug 325 may be removed by the tether 326 and it is undesirable for the tether jacket to bear any tensile load. Instead, the strength members 328 and 327 of the tether 326 pull directly on the earplug 325, ensuring that the tether jacket, which is not a strength member, is not damaged.

Referring to FIG. 1, the tether jacket 350 is stripped from the strength member 351. The two part mold 352 and 353 ends in an access point for the tether 355 to enter the sphere 354 mold. The tether strength member 351 is inserted into the mold (352 and 353) as shown in the right half of the figure and the injection mold material bonds to the tether material such that the sphere, when stressed, pulls on the strength member 351.

The manufacture of the bonded sphere or tether assembly may be accomplished in a number of different ways in order to ensure that the strength member of the tether is the load bearing member. For example, the tether may first be crimped with a compressible collar which is then submerged in the over molding process to create the spherical (or other shaped) distal tether end.

The previously described embodiments of the present invention offer a means for connecting a retractable but removable tether between the inside of an earcup and the outside of an earplug, to a) prevent foreign object damage of sensitive machinery b) improve double hearing protection compliance by offering an accessible means for using an earplug and a headset in conjunction with one another, and c) to provide a means of preventing performance degradations commonly encountered when using earplugs with tethers under headsets, that break the earseal of the circumaural protector. The present invention illustrates an approach to hearing protection using passive hearing protection solutions alone. It will be appreciated those skilled in the art that active noise reduction earplugs and communication earplugs may also be used in conjunction with circumaural hearing protectors of the present invention to offer the maximum amount of hearing protection and ambient noise attenuation. Placing the electronic connection point inside the earcup will offer the benefits identified above as well as the added benefit of protecting the electronic connection from harsh environments and abuse related damage such as drop, shock and snag hazards as are commonly found in harsh military environments. The retractable tether and attachment mechanism described herein may also be applied to electronically driven earplugs without departing from the scope of the present invention.

A double hearing protection device has been described. It will be understood by those skilled in the art that the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular. Moreover, a reference to a specific time, time interval, and instantiation of scripts or code segments is in all respects illustrative and not limiting.

What is claimed is:

1. A double hearing protection device comprising:
   a circumaural hearing protector, wherein the circumaural hearing protector comprises an earcup adapted for covering a pinna of a user, and wherein the earcup comprises an interior attachment point;
   an earplug device adapted for manual insertion into an ear canal of a user;
   a tether assembly, wherein the tether assembly comprises an earplug termination and an earcup termination, and wherein the tether assembly is adapted for:
      attaching to the earplug device at the earplug termination;
      removably attaching to the interior attachment point of the earcup at the earcup termination; and
      retracting for storage inside the earcup when the earcup is placed over the earplug device and over the pinna of the user.

2. The double hearing protection device of claim 1, wherein the tether assembly is coiled.

3. The double hearing protection device of claim 1, wherein the tether assembly comprises a strength member.

4. The double hearing protection device of claim 3, wherein the strength member is selected from the group consisting of aramid and Kevlar.

5. The double hearing protection device of claim 1, wherein the interior attachment point comprises a spherical chamber, wherein the earcup termination comprises a spherical termination, and wherein the spherical termination is adapted to mate with the spherical chamber.

6. The double hearing protection device of claim 1, wherein the earplug device is a passive hearing protection device.

7. The double hearing protection device of claim 1, wherein the tether assembly comprises an electrical conductor, wherein the earcup and the earplug device are adapted to exchange electrical signals via the electrical conductor, wherein the earcup termination comprises a first electrical connector, and wherein the interior attachment point comprises a second electrical connector adapted for mating with the first electrical connector.

8. The double hearing protection device of claim 7, wherein the electrical signals comprise audio signals generated by an audio source and wherein the earplug device comprises a transducer adapted for receiving the audio signals.

9. The double hearing protection device of claim 8, wherein the electrical audio source is selected from a group comprising a microphone, a radio, an intercom, an amplifier, and a sound conditioning circuit.

10. The double hearing protection device of claim 1, wherein the earplug device is further adapted to provide active noise control in the ear canal.

11. The double hearing protection device of claim 1, wherein the circumaural hearing protection device further comprises a headband adapted for retaining the earcup in a position that encircles the pinna of the user, and wherein the earcup further comprises an external attaching mechanism adapted for connecting the earcup to the headband, and wherein the external attaching mechanism is adapted for:
   moving the earcup into a first position that covers the pinna of the user;
   moving the earcup into a second position displaced from the pinna of the user without removing the headband;
   locking the earcup in the first position; and
   locking the earcup in the second position.

12. The double hearing protection device of claim 11, wherein the external attaching mechanism comprises a hinge, and wherein the earcup is adapted to rotate upward relative to the pinna to the second position.

13. The double hearing protection device of claim 11, wherein the external attaching mechanism comprises a hinge, and wherein the earcup is adapted to rest orthogonally from the pinna in the second position.

14. The double hearing protection device of claim 1,
   wherein the interior attachment point comprises a first molded feature and wherein the earcup termination comprises a second molded feature, and wherein the second molded feature is adapted to mate with the first molded feature, and
   wherein the earplug termination comprises a third molded feature comprising a bend relief and wherein the third molded feature is adapted for bonding to the earplug device.

15. The double hearing protection device of claim 14, wherein the tether assembly comprises a strength member, and wherein the strength member is adapted for bonding to the second molded feature and to the earplug device.

* * * * *

UNITED STATES PATENT AND TRADEMARK OFFICE
CERTIFICATE OF CORRECTION

| | | |
|---|---|---|
| PATENT NO. | : 7,457,428 B2 | |
| APPLICATION NO. | : 11/494067 | |
| DATED | : November 25, 2008 | |
| INVENTOR(S) | : Michael A. Vaudrey et al. | |

It is certified that error appears in the above-identified patent and that said Letters Patent is hereby corrected as shown below:

Column 1, line 3, insert the following section title and paragraph before the section entitled "Background":

--GOVERNMENT RIGHTS

This invention was made with Government support under contract N0421-03-C-0009 awarded by the Department of the Navy. The Government has certain rights in this invention. The U.S. Government has a paid-up license in this invention and the right in limited circumstances to require the patent owner to license others on reasonable terms as provided by the terms of contract N0421-03-C-0009 awarded by the Department of the Navy.--

Signed and Sealed this

Twenty-fourth Day of November, 2009

David J. Kappos
*Director of the United States Patent and Trademark Office*